United States Patent
Pellicciari

(10) Patent No.: US 7,812,011 B2
(45) Date of Patent: *Oct. 12, 2010

(54) STEROID AGONIST FOR FXR

(75) Inventor: Roberto Pellicciari, Perugia (IT)

(73) Assignee: Intercept Pharmaceuticals, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/590,848

(22) PCT Filed: Feb. 28, 2005

(86) PCT No.: PCT/EP2005/002086

§ 371 (c)(1),
(2), (4) Date: Jul. 3, 2007

(87) PCT Pub. No.: WO2005/082925

PCT Pub. Date: Sep. 9, 2005

(65) Prior Publication Data

US 2008/0039435 A1    Feb. 14, 2008

(30) Foreign Application Priority Data

Feb. 26, 2004 (EP) ................... 04004408

(51) Int. Cl.
*A61K 31/57* (2006.01)
*C07J 9/00* (2006.01)
(52) U.S. Cl. ...................... 514/182; 552/551
(58) Field of Classification Search ............... 552/551; 514/182
See application file for complete search history.

(56) References Cited

FOREIGN PATENT DOCUMENTS

EP    0312867    * 4/1989
WO    WO 03/080803 A2    10/2003
WO    WO 2004/007521    1/2004

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta et al. (Advanced Drug Delivery Reviews, 48 (2001), pp. 3-26).*
Li-Zhi Mi, et al. "Structural Basis for Bile Acid Binding and Activation of the Nuclear Receptor FXR": Molecular Cell, vol. 11, 2003; pp. 1093-1100.
R. Pellicciari, et al. "6a-Ethyl-Chenodeoxycholic Acid (6-ECDCA), a Potent and Selective FXR Agonist Endowed with Anticholestatic Activity", Journal of Medicinal Chemistry, vol. 45, No. 17; Aug. 15, 2002; pp. 3569-3572.
International Search Report dated Aug. 31, 2005 for PCT/EP2005/002086.

* cited by examiner

*Primary Examiner*—Barbara P Badio
(74) *Attorney, Agent, or Firm*—Ivor R. Elrifi; Jennifer Loebach; Mintz, Levin, Cohn, Ferris, Glovsky and Popeo, P.C.

(57) ABSTRACT

The invention relates to a FXR agonist of formula (I) and pharmaceutically acceptable salts, solvates or amino acid conjugates thereof.

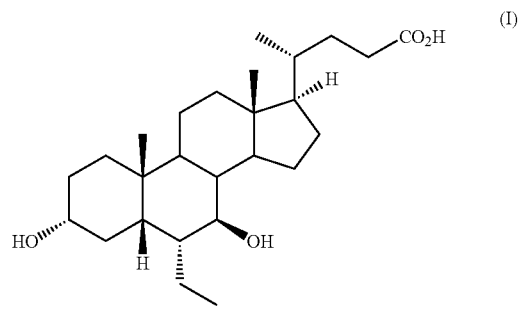

11 Claims, No Drawings

STEROID AGONIST FOR FXR

FIELD OF THE INVENTION

The present invention relates to Farnesoid X receptors (FXR). More particularly, the present invention relates to a compound useful as FXR agonist and pharmaceutical formulations containing thereof.

BACKGROUND OF THE INVENTION

Farnesoid X Receptor (FXR) is an orphan nuclear receptor initially identified from a rat liver cDNA library (B M. Forman, et al., *Cell* 81:687-693 (1995)) that is most closely related to the insect ecdysone receptor. FXR is a member of the nuclear receptor family of ligand-activated transcription factors that includes receptors for the steroid, retinoid, and thyroid hormones (D J. Mangelsdorf, et al., *Cell* 83:841-850 (1995)). Northern and in situ analysis show that FXR is most abundantly expressed in the liver, intestine, kidney, and adrenal (B M. Forman, et al., *Cell* 81:687-693 (1995) and W. Seol, et al., *Mol. Endocrinnol.* 9:72-85 (1995)). FXR binds to DNA as a heterodimer with the 9-cis retinoic acid receptor (RXR). The FXR/RXR heterodimer preferentially binds to response elements composed of two nuclear receptor half sites of the consensus AG(G/T)TCA organized as an inverted repeat and separated by a single nucleotide (IR-1 motif) (B M. Forman, et al., *Cell* 81:687-693 (1995)). An early report showed that rat FXR is activated by micromolar concentrations of farnesoids such as farnesol and juvenile hormone (B M. Forman, et al., *Cell* 81:687-693 (1995)). However, these compounds failed to activate the mouse and human FXR, leaving the nature of the endogenous FXR ligand in doubt. Several naturally-occurring bile acids bind to and activate FXR at physiological concentrations (PCT WO 00/37077, published 29 Jun. 2000)). As discussed therein, the bile acids that serve as FXR ligands include chenodeoxycholic acid (CDCA), deoxycholic acid (DCA), lithocholic acid (LCA), and the taurine and glycine conjugates of these bile acids.

Bile acids are cholesterol metabolites that are formed in the liver and secreted into the duodenum of the intestine, where they have important roles in the solubilization and absorption of dietary lipids and vitamins. Most bile acids (~95%) are subsequently reabsorbed in the ileum and returned to the liver via the enterohepatic circulatory system. The conversion of cholesterol to bile acids in the liver is under feedback regulation: bile acids down-regulate the transcription of cytochrome P450 7a (CYP7a), which encodes the enzyme that catalyzes the rate limiting step in bile acid biosynthesis. There are data to suggest that FXR is involved in the repression of CYP7a expression by bile acids, although the precise mechanism remains unclear (D W. Russell, *Cell* 97:539-542 (1999)). In the ileum, bile acids induce the expression of the intestinal bile acid binding protein (IBABP), a cytoplasmic protein which binds bile acids with high affinity and may be involved in their cellular uptake and trafficking. Two groups have now demonstrated that bile acids mediate their effects on IBABP expression through activation of FXR, which binds to an IR-1 type response element that is conserved in the human, rat, and mouse IBABP gene promoters (14; 17). Thus FXR is involved in both the stimulation (IBABP) and the repression (CYP7a) of target genes involved in bile acid and cholesterol homeostasis.

European Patent No. 0 312 867, published 5 May 1992 to Giuliana S.p.A. describes 6-methyl derivatives of natural biliary acids such as ursodeoxycholic acid, ursocholic acid, chenodeoxycholic acid and cholic acid.

WO 02/072598 discloses cholanoic acid derivatives having the following structure:

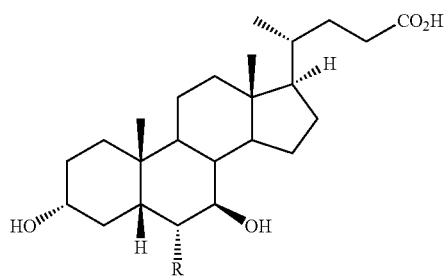

wherein R is ethyl, propyl and allyl.

BRIEF SUMMARY OF THE INVENTION

According to a first aspect, the present invention provides a compound of formula (I):

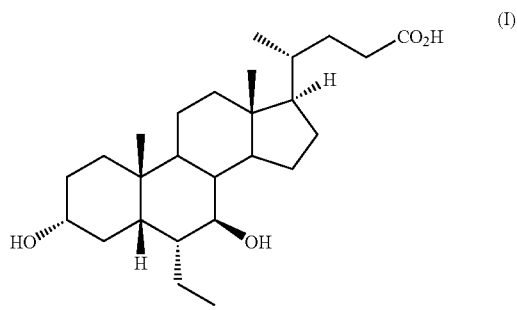

and pharmaceutically acceptable salts, solvates or amino acid conjugates thereof. In one preferred embodiment, the compound of formula (I) is in the form of the glycine or taurine conjugate.

In another aspect, the present invention provides a compound which is a FXR agonists.

In another aspect, the present invention provides a pharmaceutical formulation comprising the compound of formula (I) and a pharmaceutically acceptable carrier or diluent.

In another aspect, the present invention provides a method for the prevention or treatment of an FXR mediated disease or condition. The method comprises administering a therapeutically effective amount of the compound of formula (I). The present invention also provides the use of the compound of formula (I) for the preparation of a medicament for the prevention or treatment of an FXR mediated disease or condition.

In another aspect, the present invention provides a method for the prevention or treatment of cardiovascular disease. The method comprises administering a therapeutically effective amount of the compound of formula (I). The present invention also provides the use of the compound of formula (I) for the preparation of a medicament for the prevention or treatment of cardiovascular disease. In one embodiment, the cardiovascular disease is atherosclerosis.

In another aspect, the present invention provides a method for increasing HDL cholesterol. The method comprises administering a therapeutically effective amount of the compound of formula (I). The present invention also provides the use of the compound of formula (I) for the preparation of a medicament for increasing HDL-cholesterol.

In another aspect, the present invention provides a method for lowering triglycerides. The method comprises administering a therapeutically effective amount of the compound of formula (I). The present invention also provides the use of the compound of formula (I) for the preparation of a medicament for lowering triglycerides.

In another aspect, the present invention provides a method for the prevention or treatment of cholestatic liver disease. The method comprises administering a therapeutically effective amount of the compound of formula (I). The present invention also provides the use of the compound of formula (I) for the preparation of a medicament for the prevention or treatment of cholestatic liver diseases.

In another aspect, the present invention provides a radiolabeled compound of formula (I). In one embodiment, the compound of formula (I) is tritiated.

In another aspect, the present invention provides a process for preparing the compound of formula (I) and pharmaceutically acceptable salts, solvates or amino acid conjugates thereof. The process comprises the steps of:

a) reacting 3α-hydroxy-7-keto-5β-cholan-24-oic acid methyl ester (II)

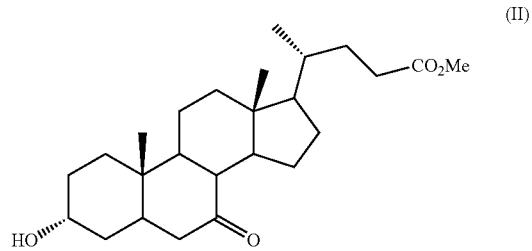

(II)

with trimethylsilylchloride (TMSCl) to prepare 3α, 7-dimethylsilyloxy-5β-chol-6en-24-oate (III);

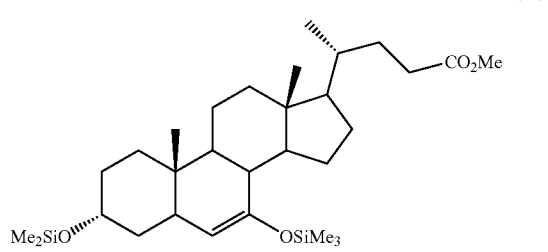

(III)

b) reacting (III) with acetaldehyde to prepare a compound of formula (IV)

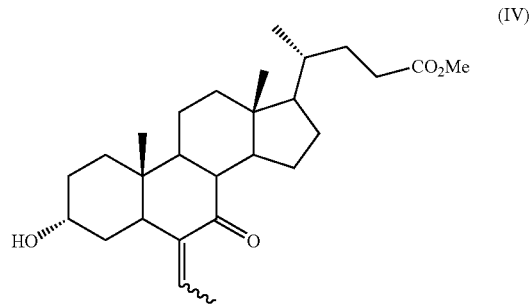

(IV)

c) submitting the compound of formula (IV) to catalytic reduction to prepare a compound of formula (V)

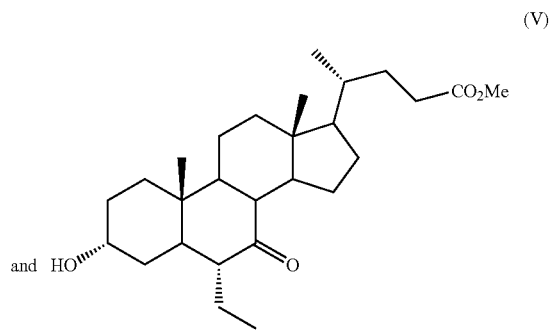

(V)

and d) submitting compound (V) to hydrolysis and reduction to obtain the compound of formula (I).

Further aspects of the present invention are described in the detailed description of the invention, examples, and claims which follow.

DETAILED DESCRIPTION OF THE INVENTION

The present invention provides a compound of formula (I):

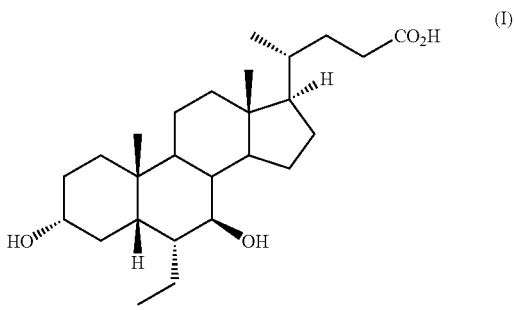

(I)

and pharmaceutically acceptable salts, solvates or amino acid conjugates thereof.

Suitable pharmaceutically acceptable salts according to the present invention will be readily determined by one skilled in the art and will include, for example, basic salts such as metallic salts made from aluminium, calcium, lithium, magnesium, potassium, sodium, and zinc or organic salts made from N,N'-dibenzylethylenediamine, chlorprocaine, choline, diethanolamine, ethylendiamine, meglumine (N-methylglucamine), and procaine. Such salts may be prepared using conventional techniques, from the compound of formula (I) by reacting, for example, the appropriate base with the compound of formula (I).

When used in medicine, the salts of the compound of formula (I) should be pharmaceutically acceptable, but pharmaceutically unacceptable salts may conveniently be used to prepare the corresponding free base or pharmaceutically acceptable salts thereof.

As used herein, the term "solvate" is a crystal form containing the compound of formula (I) or a pharmaceutically acceptable salt thereof and either a stoichiometric or a non-stoichiometric amount of a solvent. Solvents, by way of example, include water, methanol, ethanol, or acetic acid. Hereinafter, reference to a compound of formula (I) is to any physical form of that compound, unless a particular form, salt or solvate thereof is specified.

As used herein, the term "amino acid conjugates" refers to conjugates of the compound of formula (I) with any suitable amino acid. Preferably, such suitable amino acid conjugates of the compound of formula (I) will have the added advantage of enhanced integrity in bile or intestinal fluids. Suitable amino acids include but are not limited to glycine and taurine. Thus, the present invention encompasses the glycine and taurine conjugates of the compound of formula (I).

Hereinafter all references to "the compound of formula (I)" refer to the compound of formula (I) as described above together with pharmaceutically acceptable salts, solvates or amino acid conjugates thereof.

The compound of formula (I) is a FXR agonist. As used herein, the term "agonist" refers to compounds which achieve at least 50% activation of FXR relative to CDCA, the appropriate positive control in the assay methods described in PCT Publication No. WO 00/37077 published 29 Jun. 2000 to Glaxo Group Limited, the subject matter of which is incorporated herein by reference in its entirety. More preferably, the compound of this invention achieves 100% activation of FXR in the scintillation proximity assay or the HTRF assay as described in PCT Publication No. WO 00/37077.

The compound of formula (I) is useful for a variety of medicinal purposes. The compound of formula (I) may be used in methods for the prevention or treatment of FXR mediated diseases and conditions. FXR mediated diseases or conditions include cardiovascular diseases such as atherosclerosis, arteriosclerosis, hypercholesteremia, and hyperlipidemia. In particular, the compound of formula (I) is useful in the treatment and prevention of cardiovascular disease including atherosclerosis and hypercholesteremia. The compound of formula (I) is also useful for increasing HDL-cholesterol and lowering triglycerides.

In addition, the compound of the present invention is useful for the prevention and treatment of cholestatic liver diseases, since it increases the flow of bile acid. Increased flow of bile acids improves the flux of bile acids from the liver to the intestine (C. Sinal, *Cell* 102: 731-744 (2000)). Essentially, FXR null mice demonstrate that FXR plays a central role in bile acid homeostasis, and is therefore critical to lipid homeostasis by virtue of the regulation of enzymes and transporters that are critical to lipid catabolism and excretion. FXR therefore is an important target for the treatment of a number of choestatic liver disease and other lipid related diseases and conditions.

The methods of the present invention are useful for the treatment of mammals generally and particularly humans.

The methods of the present invention comprise the step of administering a therapeutically effective amount of the compound of formula (I). As used herein, the term "therapeutically effective amount" refers to an amount of the compound of formula (I) which is sufficient to achieve the stated effect. Accordingly, a therapeutically effective amount of a compound of formula (I) used in the method for the prevention or treatment of FXR mediated diseases or conditions will be an amount sufficient to prevent or treat the FXR mediated disease or condition. Similarly, a therapeutically effective amount of a compound of formula (I) for use in the method for the prophylaxis or treatment of cholestatic liver diseases or increasing bile flow will be an amount sufficient to increase bile flow to the intestine.

The amount of a compound of formula (I) or pharmaceutically acceptable salt or solvate thereof, which is required to achieve the desired biological effect will depend on a number of factors such as the use for which it is intended, the means of administration, and the recipient, and will be ultimately at the discretion of the attendant physician or veterinarian. In general, a typical daily dose for the treatment of FXR mediated diseases and conditions, for instance, may be expected to lie in the range of from about 0.01 mg/kg to about 100 mg/kg. This dose may be administered as a single unit dose or as several separate unit doses or as a continuous infusion. Similar dosages would be applicable for the treatment of other diseases, conditions and therapies including the prophylaxis and treatment of cholestatic liver diseases.

Thus, in a further aspect, the present invention provides pharmaceutical compositions comprising, as active ingredient, a compound of formula (I) or a pharmaceutically acceptable salt or solvate thereof, together with at least one pharmaceutical carrier or diluent. These pharmaceutical compositions may be used in the prophylaxis and treatment of the foregoing diseases or conditions and in cardiovascular therapies as mentioned above.

The carrier must be pharmaceutically acceptable and must be compatible with, i.e. not have a deleterious effect upon, the other ingredients in the composition. The carrier may be a solid or liquid and is preferably formulated as a unit dose formulation, for example, a tablet which may contain from 0.05 to 95% by weight of the active ingredient. If desired, other physiologically active ingredients may also be incorporated in the pharmaceutical compositions of the invention.

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the disease or condition being treated or the nature of the therapy being used and on the nature of the active compound, but where possible, oral administration is preferred for the prevention and treatment of FXR mediated diseases and conditions.

Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising the active compound and, typically a flavoured base, such as sugar and acacia or tragacanth and pastilles comprising the active compound in an inert base, such as gelatine and glycerine or sucrose acacia.

Formulations suitable for parenteral administration typically comprise sterile aqueous solutions containing a predetermined concentration of the active compound; the solution is preferably isotonic with the blood of the intended recipient. Additional formulations suitable for parenteral administration include formulations containing physiologically suitable co-solvents and/or complexing agents such as surfactants and cyclodextrins. Oil-in-water emulsions are also suitable formulations for parenteral formulations. Although such solutions are preferably administered intravenously, they may also be administered by subcutaneous or intramuscular injection.

Formulations suitable for rectal administration are preferably provided as unit-dose suppositories comprising the active ingredient in one or more solid carriers forming the suppository base, for example, cocoa butter.

Formulations suitable for topical or intranasal application include ointments, creams, lotions, pastes, gels, sprays, aerosols and oils. Suitable carriers for such formulations include petroleum jelly, lanolin, polyethyleneglycols, alcohols, and combinations thereof.

Formulations of the invention may be prepared by any suitable method, typically by uniformly and intimately admixing the active compound with liquids or finely divided solid carriers or both, in the required proportions and then, if necessary, shaping the resulting mixture into the desired shape.

For example a tablet may be prepared by compressing an intimate mixture comprising a powder or granules of the active ingredient and one or more optional ingredients, such as a binder, lubricant, inert diluent, or surface active dispersing agent, or by moulding an intimate mixture of powdered active ingredient and inert liquid diluent.

Suitable formulations for administration by inhalation include fine particle dusts or mists which may be generated by means of various types of metered dose pressurised aerosols, nebulisers, or insufflators.

For pulmonary administration via the mouth, the particle size of the powder or droplets is typically in the range 0.5-10 µm, preferably 1-5 µm, to ensure delivery into the bronchial tree. For nasal administration, a particle size in the range 10-500 µm is preferred to ensure retention in the nasal cavity.

Metered dose inhalers are pressurised aerosol dispensers, typically containing a suspension or solution formulation of the active ingredient in a liquefied propellant. During use, these devices discharge the formulation through a valve adapted to deliver a metered volume, typically from 10 to 150 µl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol surfactants, such as oleic acid or sorbitan trioleate, anti-oxidants and suitable flavouring agents.

Nebulisers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulisers consist of the active ingredient in a liquid carrier and comprising up to 40% w/w of the formulation, preferably less than 20% w/w. The carrier is typically water or a dilute aqueous alcoholic solution, preferably made isotonic with body fluids by the addition of, for example, sodium chloride. Optional additives include preservatives if the formulation is not prepared sterile, for example, methyl hydroxy-benzoate, anti-oxidants, flavouring agents, volatile oils, buffering agents and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

In addition to the ingredients specifically mentioned above, the formulations of the present invention may include other agents known to those skilled in the art of pharmacy, having regard for the type of formulation in issue. For example, formulations suitable for oral administration may include flavouring agents and formulations suitable for intranasal administration may include perfumes.

Therefore, according to a further aspect of the present invention, there is provided the use of the compound of formula (I) in the preparation of a medicament for the prevention or treatment of FXR mediated diseases or conditions.

The compounds of the invention can be made according to any suitable method of organic chemistry. According to one method, the compound of formula (I) is prepared using the process depicted in Scheme:

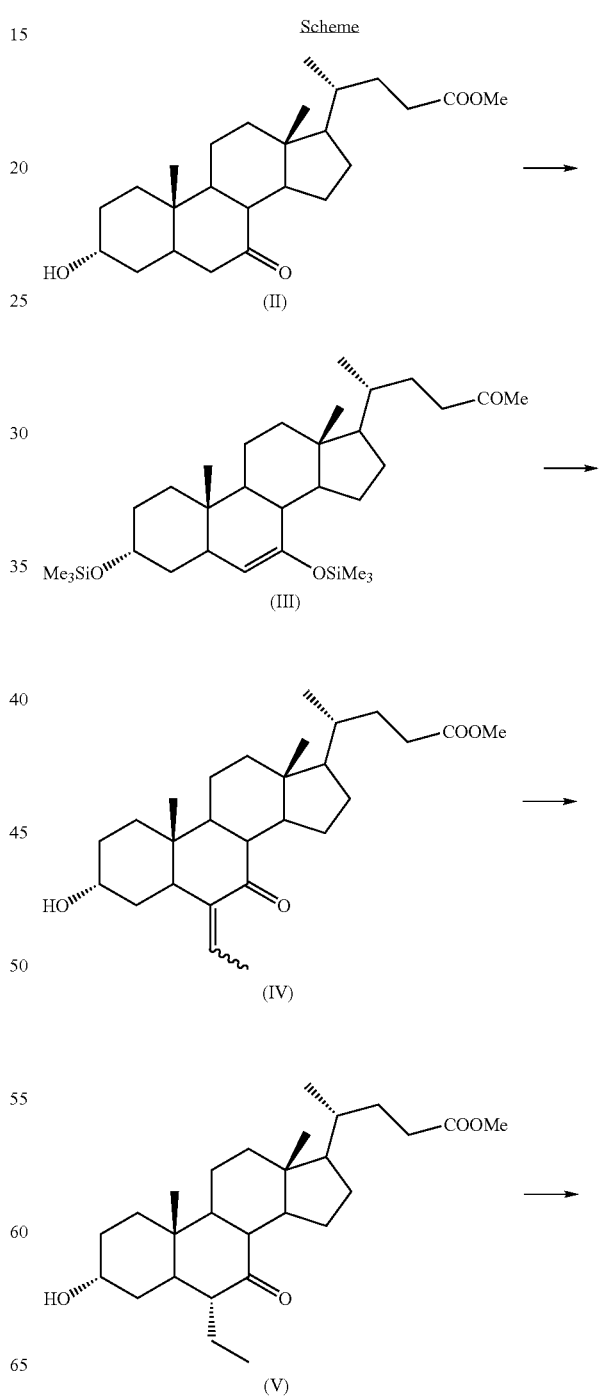

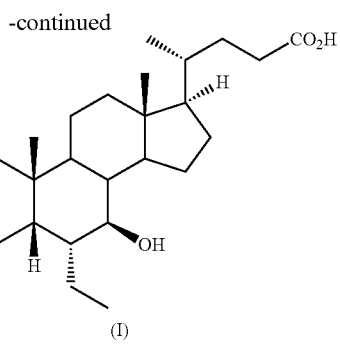

which comprises a) reacting 3α-hydroxy-7-keto-5β-cholan-24-oic acid methyl ester (II) with TMSCl to prepare 3α,7-dimethylsilyloxy-5β-chol-6en-24-oate (III); b) reacting (III) with acetaldehyde to prepare a compound of formula (IV); c) submitting the compound of formula (IV) to catalytic reduction to prepare a compound of formula (V) and d) submitting compound (V) to hydrolysis and reducing the 7-cheto group to obtain the compound of formula (I).

More particularly, 3α,7-dimethylsilyloxy-5β-chol-6en-24-oate (III) is prepared by reacting α-hydroxy-7-keto-5β-cholan-24-oic acid methyl ester (II) with TMSCl in the presence of LDA and triethylamine in THF; compound (IV) is prepared by reacting compound (III) with acetaldehyde in the presence of boron trifluoride diethyl etherate in dichloromethane; catalytic reduction of compound (IV) to compound (V) is conveniently carried out by using $PtO_2$ as the catalyst; the hydrolysis of the ester group is carried out with bases, preferably NaOH and the reduction of the 7-cheto group is carried out with sodium.

Pharmaceutically acceptable salts, solvates and amino acid conjugates of the compound of formula (I) can be prepared from the free base using methods known to those skilled in the art.

The present invention also provides radiolabeled compounds of formula (I). Radiolabeled compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I). In one preferred embodiment, the compound of formula (I) is tritiated.

The radiolabeled compounds of formula (I) are useful in assays for the identification of compounds which interact with FXR such as those described in PCT Publication No. WO 00/37077 already incorporated herein.

The following examples illustrate the invention.

EXAMPLES

Example 1

Synthesis of 3α-7-ditrimethylsyliloxy-5β-chol-6-en-24-oate methyl ester (III)

A solution of n-BuLi 2.5 M in hexane (632.3 ml, 1.58 mol) was added dropwise to a solution of diisopropylamine (217 ml, 1.66 mol) in dry THF (1250 ml) at −78° C. under nitrogen atmosphere. After 0.5 h trimethylchlorosylane (357.3 ml, 1.926 mol) was added and the resulting mixture was reacted for 15'. A solution of substrate (100 g, 0.247 mol) in dry THF (500 ml) was added dropwise in 1.5 h and after 0.5 h the mixture was treated with triethylamine (476.5 ml, 3.55 mol).

After 1 h the reaction mixture was allowed to warm to −20° C. and treated with and aqueous saturated solution of $NaHCO_3$ (500 ml), then brought up to room temperature in 3 h. The organic phase was separated and aqueous phase was extracted with ethyl acetate (2×300 ml). The combined organic phases were washed with saturated solution of $NaHCO_3$ (15 l), water (10 l) and brine (8 l). After drying over anhydrous $Na_2SO_4$ the residue was evaporated under vacuum affording 134.15 g of desired compound (III).

$^1$H-NMR (CDCl$_3$) δ: 0.0-0.2 (18H, m, 3-OSiMe$_3$ e 7-OSiMe$_3$); 0.65 (3H, s, 18-CH$_3$); 0.80 (3H, s, 19-CH$_3$); 0.95 (3H, d, 21-CH$_3$); 3.50 (1H, m, 3-CH); 3.68 (3H, s, —CO$_2$CH$_3$); 4.70 (1H, dd, 6-CH).

Example 2

Synthesis of methyl 3α-hydroxy-6-ethylidene-7-cheto-5β-cholan-24-oate (IV)

A solution of boron trifluoride diethyl etherate (113.92 ml, 0.928 mol) in 203 ml of dichloromethane was added to a cooled (−30° C.) and stirred solution of acetaldehyde (23.89 ml, 0.58 mol) and compound (II) (127.4 g, 0.232 mol) in 297 ml of dichloromethane. The reaction mixture was stirred for further 60' at −30° C. and allowed to warm to 0° C., treated with 290 ml of diethyl ether and stirred overnight at room temperature. The reaction mixture was quenched with a saturated aqueous solution of $NaHCO_3$ (500 ml). The organic phase was separated and the aqueous phase was extracted with dichloromethane (2×200 ml). The combined organic extracts were washed with a saturated aqueous solution of $NaHCO_3$ (4×250 ml) and brine (2×200 ml), then dried over anhydrous $Na_2SO_4$ and concentrated under vacuum. The residue was purified by flash chromatography on silica gel using petroleum ether: ethyl acetate (7:3, v/v) as eluent to afford 67 g of pure compound (IV) (67% yield).

$^1$H-NMR (CDCl$_3$) δ: 0.65 (3H, s, 18-CH$_3$); 0.91 (3H, d, 21-CH$_3$); 0.99 (3H, s, 19-CH$_3$); 1.69-1.71 (3H, d, 2'-CH$_3$); 2.51-2.58 (1H, dd, 8-CH); 3.65 (3H, s, —CO$_2$CH$_3$); 6.11-6.21 (1H, dd, 1'-CH).

Example 3

Synthesis of 3α,7β-dihydroxy-6α-ethyl-5β-cholan-24-oic acid (I)

A solution of methyl 3α-hydroxy-6-ethylidene-7-cheto-5β-cholan-24-oate (IV) (3.0 g, 6.97 mmol) in glacial acetic acid (150 ml) was hydrogenised in the presence of platinum oxide (300 mg) at 32 psi for 12 h. The catalyst was filtered off and the filtrate was concentrated. The residue was taken up with a mixture of water and ethyl acetate and neutralized with an aqueous solution of $NaHCO_3$. The aqueous layer was separated and extracted with ethyl acetate. The combined organic phases were washed with brine, dried over anhydrous $Na_2SO_4$ and evaporated under reduced pressure.

The crude product was hydrolysed overnight using a methanol solution of sodium hydroxide (10%, 300 ml). The mixture was then concentrated under vacuum, diluted with water, acidified with HCl and extracted with ethyl acetate. The organic phases were pooled, washed with brine, dried over anhydrous $Na_2SO_4$ and evaporated under reduced pressure.

The residue was dissolved in sec-BuOH (75 ml) and sodium was slowly added to the solution. The mixture was heated for 8 h. After evaporation of the solvent the residue was diluted with water, acidified with HCl and extracted with dichloromethane. The combined organic phases were washed with brine, dried over anhydrous Na$_2$SO$_4$ and evaporated under reduced pressure.

The crude residue was purified by flash chromatography on silica gel using dichloromethane:methanol (7:3, v/v) as eluent, to afford 1.7 g (4.18 mmol, 60%) of (I).

mp: 224-226° C.

$^1$H-NMR (CDCl$_3$) δ: 0.56 (3H, s, 18-CH$_3$), 0.70-0.77 (3H, t, 6-CH$_2$—CH$_3$), 2.14-2.29 (2H, m, 23-CH$_2$), 3.10-3.15 (1H, m, 7-CH), 3.44 (1H, m, 3-CH).

$^{13}$C-NMR (CDCl$_3$) δ: 11.21, 12.24, 18.37, 20.96, 21.35, 23.48, 26.86, 28.61, 30.15, 30.51, 30.90, 34.50, 35, 28, 39.55, 40.21, 43.15, 43.42, 43.96, 54.97, 55.95, 71.87, 75.65, 179.12.

The invention claimed is:

1. A compound of formula (I):

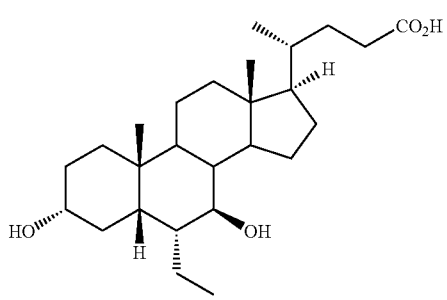

(I)

and pharmaceutically acceptable salts or amino acid conjugates thereof.

2. The glycine conjugate of the compound of formula (I):

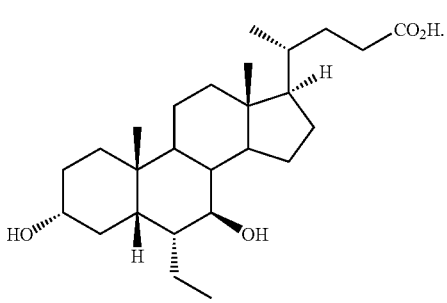

(I)

3. The taurine conjugate of the compound of formula (I):

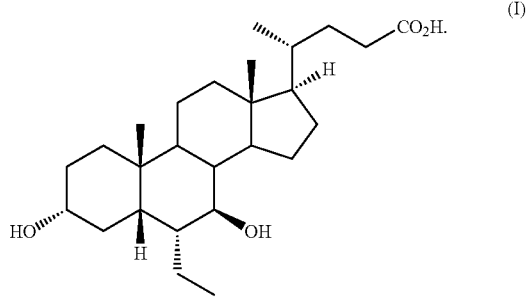

(I)

4. The compound of claim 1, wherein said compound is radiolabeled.

5. The compound of claim 4, wherein said compound is tritiated.

6. A pharmaceutical formulation comprising a compound according to claim 1 and a pharmaceutically acceptable carrier or diluent.

7. A method for the treatment of an FXR mediated disease or condition in a mammal comprising administering to a mammal suffering from an FXR mediated disease or condition a therapeutically effective amount of a compound according to claim 1, wherein said FXR mediated disease or condition is selected from the group consisting of hypercholesteremia, hyperlipidemia, low HDL-cholesterol, and high triglycerides.

8. A method for the treatment of cardiovascular disease in a mammal comprising administering to a mammal suffering from a cardiovascular disease a therapeutically effective amount of a compound according to claim 1, wherein said cardiovascular disease is selected from the group consisting of artherosclerosis and hypercholesteremia.

9. The method according to claim 8, wherein said cardiovascular disease is artherosclerosis.

10. A method for increasing HDL cholesterol in a mammal, said method comprising administering to a mammal whose HDL cholesterol is to be increased a therapeutically effective amount of a compound according to claim 1.

11. A method for lowering triglycerides in a mammal, said method comprising administering to a mammal whose triglycerides are to be lowered a therapeutically effective amount of a compound according to claim 1.

* * * * *